(12) United States Patent
Thai

(10) Patent No.: US 10,524,878 B2
(45) Date of Patent: Jan. 7, 2020

(54) MATRIX BAND SHAPING DEVICE

(71) Applicant: Hung M. Thai, San Jose, CA (US)

(72) Inventor: Hung M. Thai, San Jose, CA (US)

(*) Notice: Subject to any disclaimer, the term of this patent is extended or adjusted under 35 U.S.C. 154(b) by 0 days.

(21) Appl. No.: 15/980,414

(22) Filed: May 15, 2018

(65) Prior Publication Data

US 2019/0350678 A1    Nov. 21, 2019

(51) Int. Cl.
*A61C 5/85*    (2017.01)

(52) U.S. Cl.
CPC ..................... *A61C 5/85* (2017.02)

(58) Field of Classification Search
CPC .... A61C 5/85; A61C 3/00; A61C 3/10; A61C 7/04; B25B 7/02; B25B 7/22; A61B 17/282
USPC .... 433/226; 81/418–417, 424.5, 426, 426.5; 101/3.1
See application file for complete search history.

(56) References Cited

U.S. PATENT DOCUMENTS

| | | | |
|---|---|---|---|
| 340,896 A | 4/1886 | Starr | |
| 816,828 A | 3/1906 | Smith | |
| 1,688,670 A | 10/1928 | Swendiman | |
| 2,123,475 A | 7/1938 | Sachs | |
| 2,698,483 A | 1/1955 | Berkowitz | |
| 3,305,928 A | 2/1967 | Tofflemire | |
| 3,521,510 A | 7/1970 | Angquist | |
| 3,626,995 A | 12/1971 | Keenan, Jr. | |
| 4,081,909 A | 4/1978 | Garcia | |
| 4,563,152 A * | 1/1986 | McClure | A61C 5/85 432/142 |
| 5,330,353 A | 7/1994 | Wavrin | |
| 6,336,387 B1 | 1/2002 | Lee | |
| 6,345,983 B1 | 2/2002 | Godfrey | |
| 6,712,608 B2 | 3/2004 | Bills | |
| 2003/0224324 A1 | 12/2003 | Dryer | |
| 2004/0106084 A1 | 6/2004 | Dryer | |
| 2008/0294190 A1 | 11/2008 | Young | |
| 2017/0065371 A1* | 3/2017 | Ferrer | A61C 3/00 |

* cited by examiner

*Primary Examiner* — Heidi M Eide
*Assistant Examiner* — Mirayda A Aponte

(57) ABSTRACT

A dental device for shaping matrix bands. The device has a first arm pivotally connected to a second arm. A male head component having a curved, convex inner sidewall with a flattened surface centrally disposed thereon is connected to a bar portion of the first arm. A female head component having a curved, concave inner sidewall with a flattened surface centrally disposed thereon is connected to a bar portion of the second arm. When a handle portion of the first arm is pivoted towards a handle portion of the second arm, the first bar portion pivots toward the second bar portion. The male head component mates with the female head component such that the inner sidewall of the male head component interfaces with the inner sidewall of the female head component, and the flattened surface of the male head component interfaces with the flattened surface of the female head component.

9 Claims, 6 Drawing Sheets

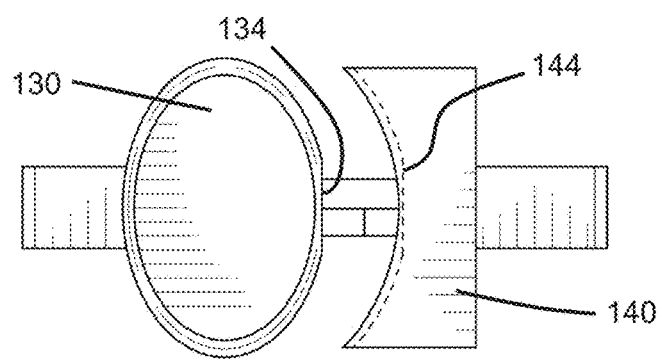
FIG. 2
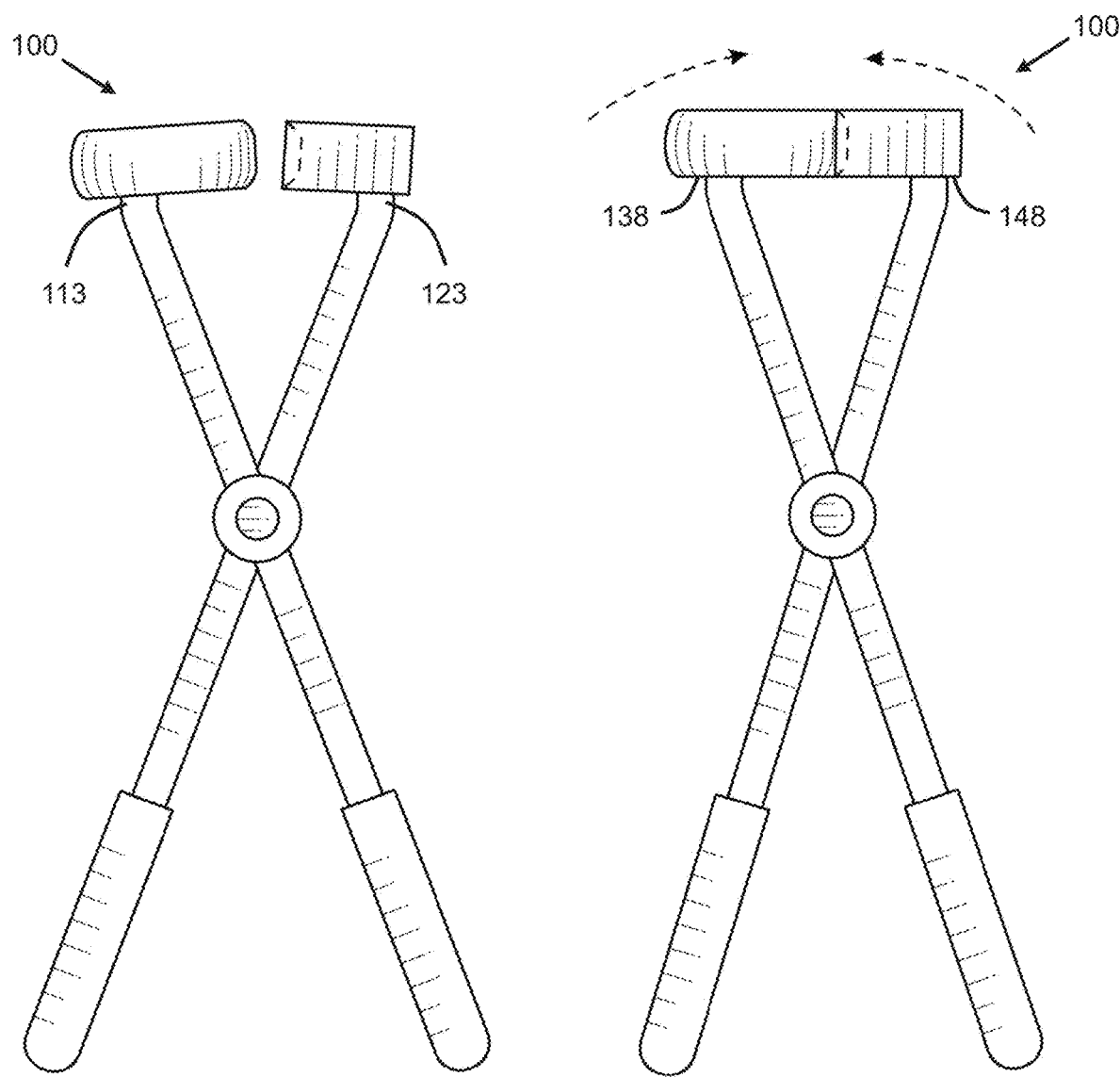
FIG. 3A
FIG. 3B

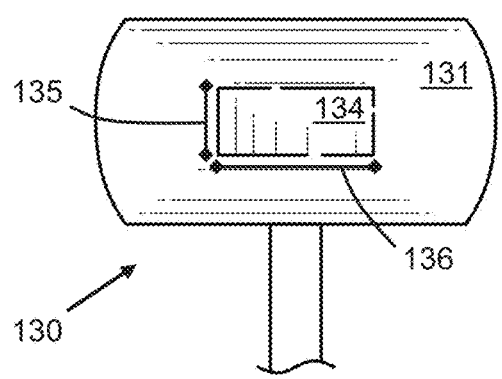
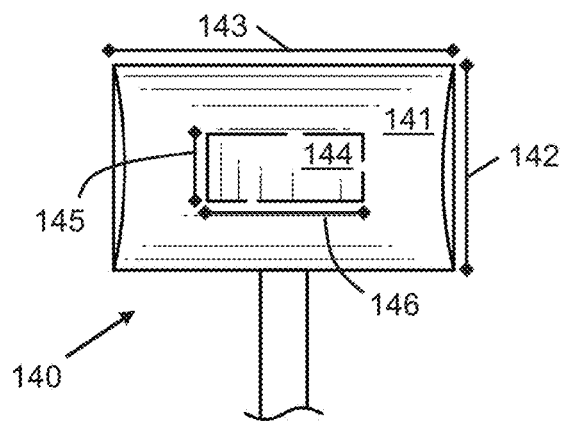
FIG. 4A
FIG. 4B
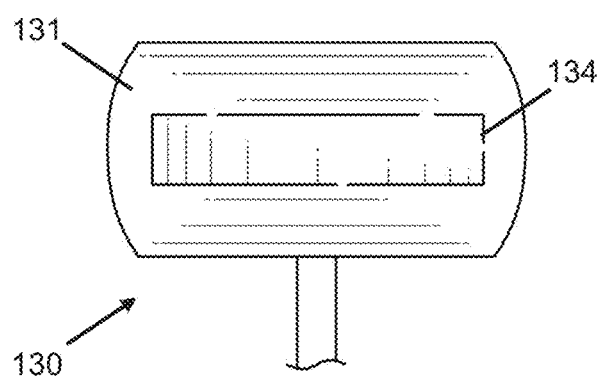
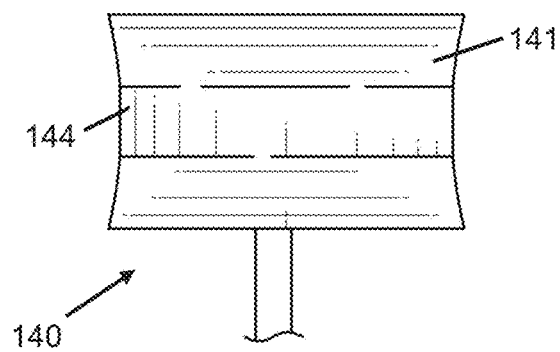
FIG. 5A
FIG. 5B
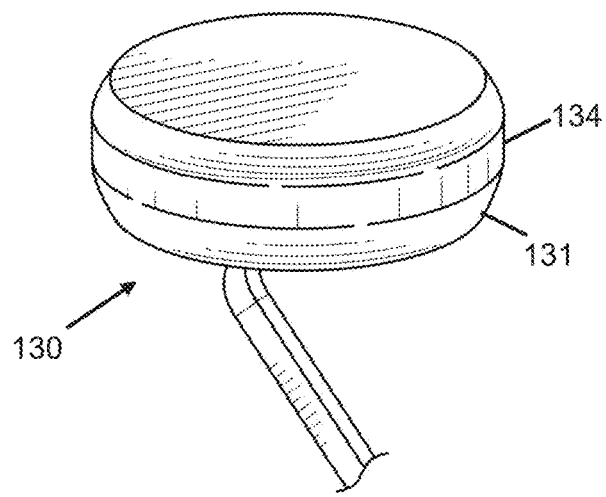
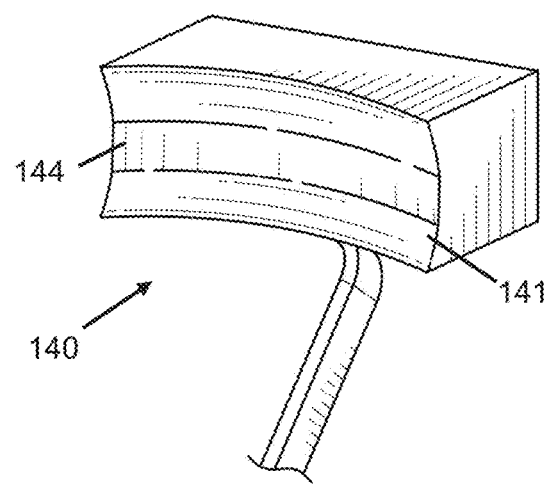
FIG. 6A
FIG. 6B

MATRIX BAND SHAPING DEVICE

FIELD OF THE INVENTION

The present invention is directed to a dental accessory, more particularly, to a device for shaping and fitting a matrix band securely to a tooth.

BACKGROUND OF THE INVENTION

Dental caries, also referred to as tooth decay, are permanently damaged structures of the tooth that are typically caused by plaque, bacteria, excessive sugar consumption, and improper or inadequate oral hygiene. Cavities caused by the tooth decay/caries often require treatment by restoration of the decayed tooth. During treatment, a dentist generally uses a dental hand piece and dental burs to remove all of the decayed structure from the tooth. After removing the caries, the tooth is left having a cavity. The dentist will place a dental matrix band around the tooth to provide temporary structural support, e.g. wall, to the cavity. The cavity is then filled with a dental filling material, such as composite resins, cement, ceramics, or dental amalgams, which is allowed to cure and set, thereby re-establishing the tooth structure.

Dental matrix bands are used to restore anatomic contours and contact areas of the tooth. Existing matrix bands used in dentistry today are typically metallic strips that may have a flat surface or concaved contour. A flat matrix band may be burnished or shaped to add a concaved contour. For example, U.S. Pat. No. 4,081,909 of Garcia discloses an orthodontic plier for bending orthodontic arch wires. If a matrix band is shaped with the plier of Garcia, the band would acquire a concaved contour. As shown in FIG. 9, one disadvantage of a concaved contour is that it creates a rounded point of contact to an adjacent tooth. This rounded point of contact lacks stability and is more prone to breaking, thus the filling will require future restoration. Hence there is a need for a dental device that allows for improved contouring of the matrix band.

The present invention features a novel dental tool for shaping and fixing matrix bands securely to a tooth. Generally, the shaping device of the present invention resembles a pair of pliers, which allows a dentist to form a customized contour surface into the traditional matrix band prior to placing the matrix band around the tooth.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide for dental device and methods for shaping a matrix band, as specified in the independent claims. Embodiments of the invention are given in the dependent claims. Embodiments of the present invention can be freely combined with each other if they are not mutually exclusive.

In some aspects, the present invention features a dental device comprising a first arm having a first bar portion connected to a first handle portion and a first pivot point disposed between the first bar portion and the first handle portion, a second arm having a second bar portion connected to a second handle portion and a second pivot point disposed between the second bar portion and the second handle portion, a male head component disposed on a terminal end of the first bar portion, and a female head component disposed on a terminal end of the second bar portion. The first arm may be pivotably connected to the second arm by a pivot. The male head component can have a curved, convex inner sidewall oriented to face a curved, concave inner sidewall of the female head component. A first flattened surface disposed on a midsection of the inner sidewall of the male head component may be aligned with and facing a second flattened surface disposed on a midsection of the inner sidewall of the female head component. When the arms of the device is pivoted into a closed configuration, the male head component mates with the female head component such that the curved, convex inner sidewall of the male head component interfaces with the curved, concave inner sidewall of the female head component, and the first flattened surface of the male head component is directly interfacing with the second flattened surface of the female head component.

In other aspects, the method of shaping a matrix band may comprise pivoting the dental device into an open configuration, placing or positioning the matrix band between the male head component and the female head component, pivoting the dental device into the closed configuration, and applying pressure to the male head component and the female head component so as to compress the matrix band between the head components. Thus, the matrix band is shaped or formed to have i) a contour and curvature similar to that of the inner sidewall of the female head component, and ii) a flattened surface similar to the second flattened surface and disposed on a midsection of the matrix band, or any specific section of the matrix band depending on a preference of the dentist and/or contour of the tooth.

In another aspect, the dental device may be used during a restoration procedure for restoring a tooth having caries. The method may comprise removing the caries from the tooth thereby forming at least one cavity in the tooth, shaping a matrix band with the dental device, placing the shaped matrix band at least partially around the tooth so as to provide structural support to the cavity and filling the cavity with a dental filler material. Preferably, the flattened surface of the matrix band is positioned adjacent to a neighboring tooth so as to form a broad, flat surface to a restored portion of the tooth that contacts or is adjacent to the neighboring tooth.

One of the unique and inventive technical features of the present invention is the flattened surface disposed on the inner sidewall of the head components. Without wishing to limit the invention to any theory or mechanism, it is believed that the technical feature of the present invention advantageously forms a flattened surface on a midsection the matrix band, which when used during the tooth restoration procedure, forms the broad, flat contact surface (i.e. horizontal and vertical dimension) on the restored portion of the tooth. This broad, flat contact surface can have increased stability as compared to a rounded point of contact, which can extend the lifetime of the restored portion. None of the presently known prior references or work has the unique inventive technical feature of the present invention.

Analogous to the contact points between spheres and the contact points between square bricks, the additional benefits of the present invention include the following:

1. Provide better protection against food trapping between teeth.

2. Teeth with broad, flat contact surfaces are more stable than ones with pointed contacts. To illustrate this mechanism, a row of square bricks is less prone to moving and shifting than a row of balls aligned with each other.

3. Restored teeth with broad, flat contact surfaces are less prone to breaking or loosening than those restored teeth with pointed or round contact surfaces, shown in FIG. 9.

BRIEF DESCRIPTION OF THE DRAWINGS

The features and advantages of the present invention will become apparent from a consideration of the following detailed description presented in connection with the accompanying drawings in which:

FIG. 2 shows a top view of the shaping tool.

FIG. 3A shows a side view of the shaping tool in an open configuration.

FIG. 3B shows a side view of the shaping tool in a closed configuration.

FIG. 4A shows front view of a male head component of the shaping tool.

FIG. 4B shows front view of a female head component of the shaping tool.

FIG. 5A shows front view of an alternative embodiment of the male head component.

FIG. 5B shows front view of an alternative embodiment of the female head component.

FIG. 6A shows another alternative embodiment of the male head component.

FIG. 6B shows another alternative embodiment of the female head component.

DESCRIPTION OF PREFERRED EMBODIMENTS

Figure 1A:
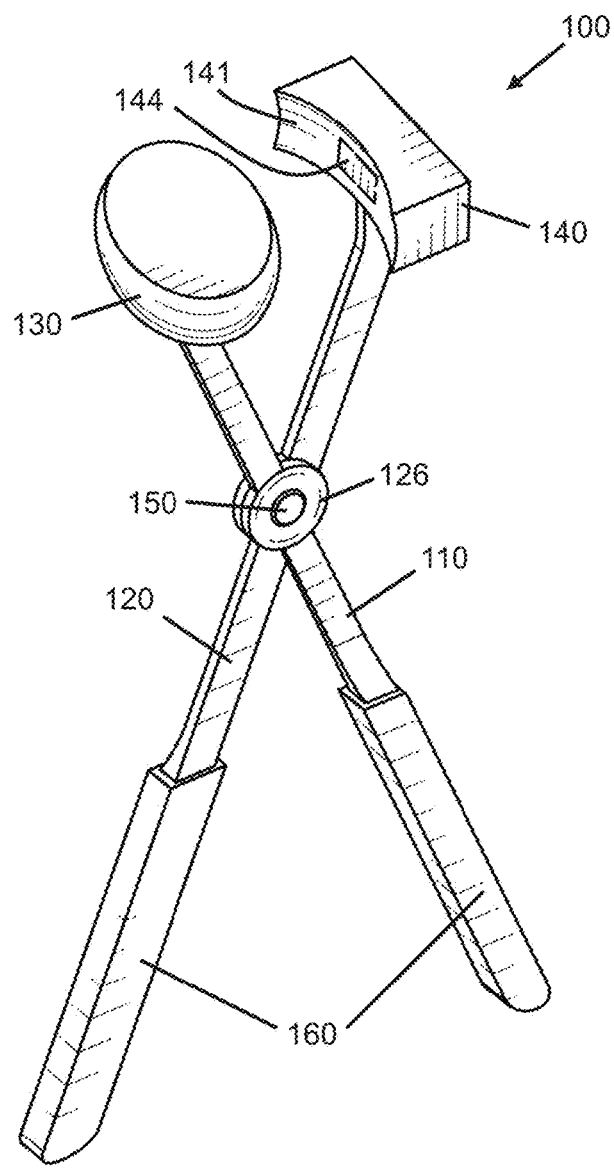
FIG. 1A shows a perspective view of a matrix band shaping tool of the present invention.
Figure 1B:
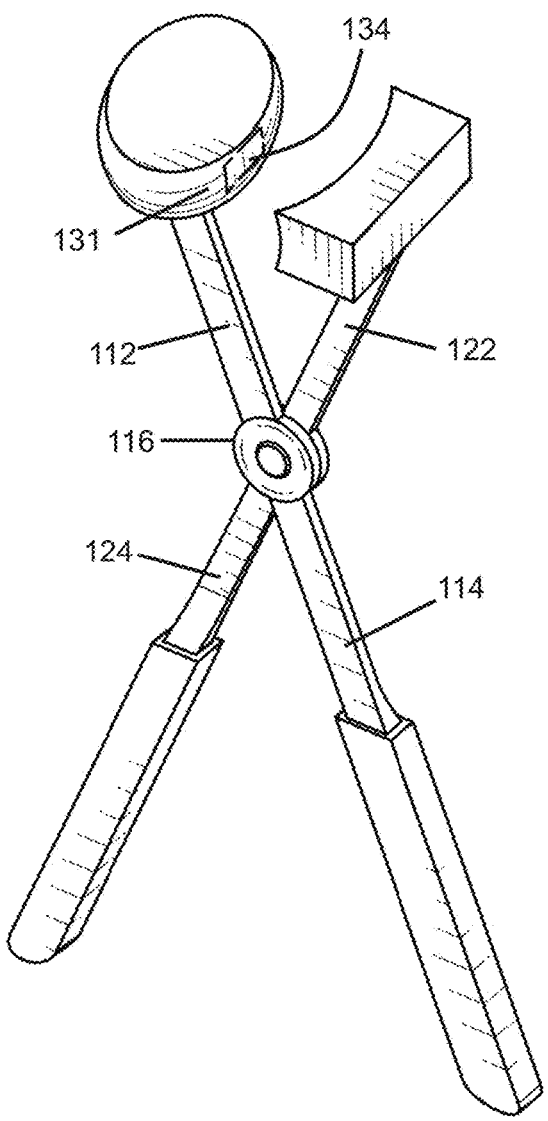
FIG. 1B shows another perspective view of a matrix band shaping tool of the present invention.
Figure 7A:
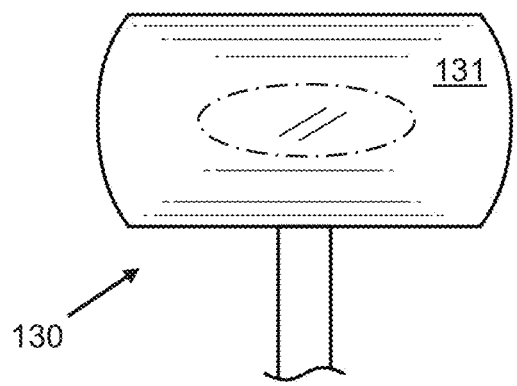
FIG. 7A shows an alternative embodiment, wherein the flattened surface of the male head component can be an oval shape.
Figure 7B:
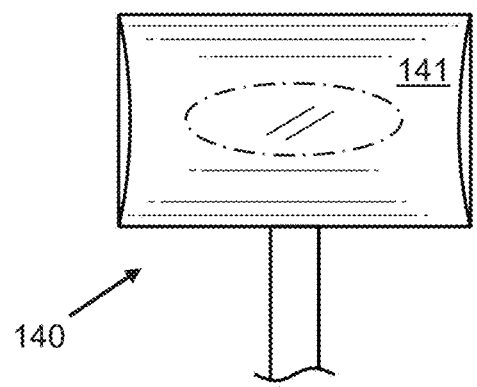
FIG. 7B shows an alternative embodiment, wherein the flattened surface of the female head component can be an oval shape.
Figure 7C:
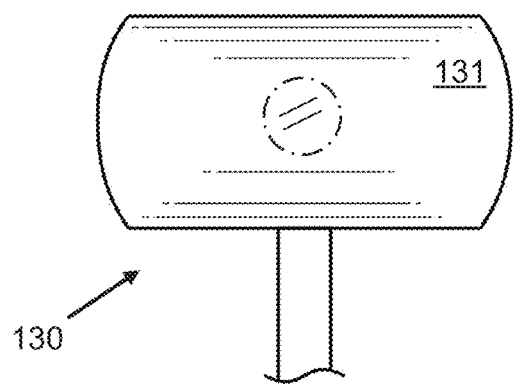
FIG. 7C shows an alternative embodiment, wherein the flattened surface of the male head component can be a circular shape.
Figure 7D:
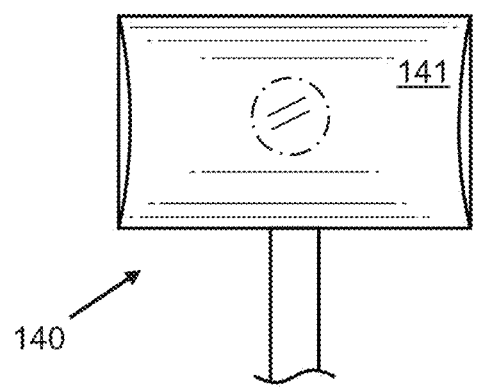
FIG. 7D shows an alternative embodiment, wherein the flattened surface of the female head component can be a circular shape.
Figure 7E:
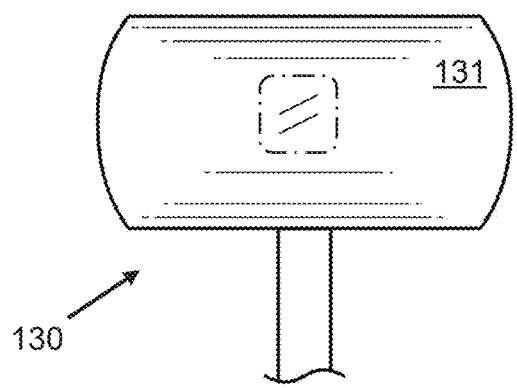
FIG. 7E shows an alternative embodiment, wherein the flattened surface of the male head component can be square shape.
Figure 7F:
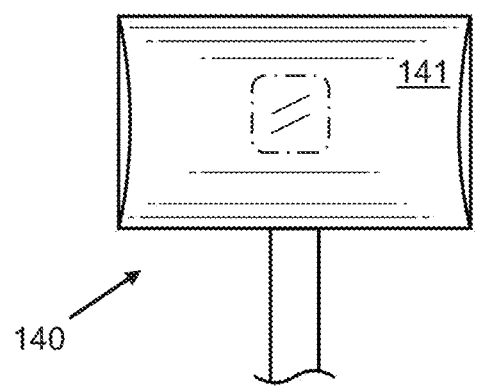
FIG. 7F shows an alternative embodiment, wherein the flattened surface of the female head component can be square shape.

Following is a list of elements corresponding to a particular element referred to herein:

10 matrix band
15 matrix band inner surface
17 flattened surface
100 dental device
110 first arm
112 first bar portion
113 terminal end of first bar portion
114 first handle portion
116 first pivot point
120 second arm
122 second bar portion
123 terminal end of second bar portion
124 second handle portion
126 second pivot point
130 male head component
131 inner sidewall of male head component
134 first flattened surface
135 height of the first flattened surface
136 width of the first flattened surface
138 bottom surface of the male head component
140 female head component
141 inner sidewall of female head component
142 height of the inner sidewall
143 width of the inner sidewall
144 second flattened surface
145 height of the second flattened surface
146 width of the second flattened surface
148 bottom surface of the female head component
1150 pivot
160 gripping section Referring now to FIG. 1A-1B, the present invention features a dental device (100) for shaping a matrix band (10). The device (100) may comprise a first arm (110) comprising a first bar portion (112) connected to a first handle portion (114) and a first pivot point (116) disposed between the first bar portion (112) and the first handle portion (114), a second arm (120) comprising a second bar portion (122) connected to a second handle portion (124) and a second pivot point (126) disposed between the second bar portion (122) and the second handle portion (124), a male head (130) component disposed on a terminal end (113) of the first bar portion, and a female head component (140) disposed on a terminal end (123) of the second bar portion.

In some embodiments, the first arm (110) may be pivotably connected to the second arm (110) by a pivot (150) disposed through the first and second pivot points (116, 126). Referring now to FIGS. 3A-3B, the first and second arm (110, 120) can rotate about the pivot (150) between an open configuration and a closed configuration. As shown in FIG. 3A, the first and second handle portions (114, 124) can be pivoted away from each other thereby pivoting the first and second bar portions (112, 122) away from each other and placing place the device (100) in the open configuration. As shown in FIG. 3B, the first and second handle portions (114, 124) can be pivoted towards each other thereby pivoting the first and second bar portions (112, 122) toward each other, and placing the device (100) in the closed configuration.

In some embodiments, the male head component can have a curved, convex inner sidewall (131). In some other embodiments, the female head component can have a curved, concave inner sidewall (141). In preferred embodiments, the inner sidewall (131) of the male head component is oriented so as to face the inner sidewall (141) of the female head component. As used herein, the terms "convex" and "concave" have their usual meaning. For example, the term "convex" refers to being curved like the exterior of a circle or sphere, or having at least one interior angle measuring less than 180°. The term "concave" refers to being curved like the interior of a circle or sphere, or having at least one interior angle greater than 180°.

As shown in FIG. 3A, the terminal end (113) of the first bar portion may be connected to a bottom surface (138) of the male head component. Similarly, the terminal end (123) of the second bar portion may be connected to a bottom surface (148) of the female head component. In an alternative embodiment, the terminal end (113) of the first bar portion may be connected to an outer sidewall of the male head component. Similarly, the terminal end (123) of the second bar portion may be connected to an outer sidewall of the female head component.

As a frame of reference, a side view of the device as shown in FIG. 3A lies on an X-Y plane. In some preferred embodiments, as shown in FIG. 3A, the convex contour of the inner sidewall of the male head component matches the concave contour of the inner sidewall of the female head component when viewed from the side view. This convex contour of the inner sidewall of the head components lies on an X-Y plane. In other preferred embodiments, the curvature of the inner sidewall of the male head component matches the curvature of the inner sidewall of the female head component when viewed from a top view. Referring to FIG. 2, when looking from the top view, the curvature of the inner sidewall of the head components lies on an X-Z plane.

In some embodiments, a first flattened surface (134) is disposed on a midsection of the inner sidewall of the male head component. In some other embodiments, a second flattened surface (144) is disposed on a midsection of the inner sidewall of the female head component. In preferred embodiments, the first flattened surface (134) is aligned with and facing the second flattened surface (144). In some embodiments, when looking at a front view of the head components, the first flattened surface (134) and the second flattened surface (144) lie on a Y-Z plane. As used herein, the term "flat surface" or equivalent refers to an area lying on a two-dimensional plane. In addition to or in the alternative, a flat surface has straight contour lines in a 2-D space. For instance, the first flattened surface (134) and the second flattened surface (144) have straight contour lines on the Y-Z plane.

As used herein, the midsection is defined as middle location equidistant from a topmost point or top edge and from a lowermost point or bottom edge. As shown in FIG. 4A, the midsection of the inner sidewall of the male head component is midway between a top surface edge and a bottom surface edge of the male head component. As shown in FIG. 4B, the midsection of the inner sidewall of the female head component is midway between a top surface edge and a bottom surface edge of the female head component.

In some embodiments, when the inner sidewall (131) of the male head component is viewed from the side, the inner sidewall (131) and first flattened surface (134) form a contour comprising a first convex segment that transitions to a substantially straight segment, which transitions to a second convex segment. In similar manner, when the inner sidewall (141) of the female head component is viewed from the side, the inner sidewall (141) and second flattened surface (144) form a contour comprising a first concave segment that transitions to a substantially straight segment, which transitions to a second concave segment.

According to preferred embodiments, when the device (100) is in the closed configuration, the male head component (130) mates with the female head component (140) such that the curved, convex inner sidewall (131) of the male head component interfaces with the curved, concave inner sidewall (141) of the female head component. Further still, the first flattened surface (134) of the male head component is directly interfacing with the second flattened surface (144) of the female head component. One would appreciate that the first flattened surface (134) and the second flattened surface (144) are similar in size and shape and positioned so as to mirror each other, thus allowing for the surfaces of the inner sidewalls to have maximum surface contact and to eliminate any gaps between the surfaces of the inner sidewalls.

In some embodiments, a gripping section (160) may be disposed on the first and second handle portions (114, 124). As shown in FIG. 1B, the gripping section may cover a section extending from the ends of the handle portion. In some embodiments, the gripping section may comprise gripping tape, a cushioned grip material, a plastic sleeve snugly fitted onto the handle portions, or any material that provides a non-slip grip to the handle portions. In other embodiments, the handle portion may have smooth or textured surfaces without any material cover, depending on the dentist's preference.

In one embodiment, the male head component (130) may be generally circular or oval in shape when viewed from the top view, as shown in FIG. 2. In some embodiments, the male head component is a cylindrical structure with bulging or convex side wall. This sidewall can have a flat section corresponding to the first flattened surface.

In another embodiment, as shown in FIG. 4B, the inner sidewall (141) of the female head component may be rectangular in shape when viewed from a front view or Y-Z plane. Referring to FIG. 1A, in one embodiment, the female head component comprises a rectangular box structure having one side surface recessed into a shape of a bowl or parabola with a flat surface disposed in the depth of the recessed surface. In some embodiments, the first and second flattened surfaces (134, 144) may also be rectangular in shape. In other embodiments, as shown in FIG. 7A-7F, the flattened surfaces may be oval, circular, or square in shape.

In some embodiments, a height (145) of the second flattened surface is about ¼ to ⅔ the height (142) of the inner sidewall of the female head component. As used herein, the term "height" refers to the distance between a top edge and a bottom edge of a specified structure. Preferably, a height (135) of the first flattened surface is equal to the height (145) of the second flattened surface. For example, the height of the first and second flattened surfaces may be about ¼ to ⅔ the height of the inner sidewall of the female head component.

In other embodiments, a width (146) of the second flattened surface is about ¼ to ⅔ the width (143) of the inner sidewall of the female head component. As used herein, the term "width" refers to the distance between a first side edge and a second, opposing side edge of a specified structure. Preferably, a width (136) of the first flattened surface is equal to the width (146) of the second flattened surface. For example, the width of the first and second flattened surfaces may be about ¼ to ½ the width of the inner sidewall of the female head component.

In an alternative embodiment, as shown in FIGS. 5A and 5B, the width (146) of the second flattened surface is equal to the width (143) of the inner sidewall of the female head component. Thus, the width (136) of the first flattened surface is at least equal to the width (146) of the second flattened surface. In another alternative embodiment, as shown in FIG. 6A, the width (136) of the first flattened surface may span the entire perimeter, or circumference, of the sidewall of the male head component. Thus, as shown in FIG. 6B, the width (146) of the second flattened surface is equal to the width (143) of the inner sidewall of the female head component in order to maximize surface contact between the inner sidewalls.

In some embodiments, the width of the inner sidewall may range from about 20 mm to 40 mm. For example, the width of the inner sidewall may be about 20 mm to 30 mm. In other embodiments, the height of the inner sidewall may range from about 10 mm to 30 mm. For example, the height of the inner sidewall may be about 15 mm to 25 3 m. In some other embodiments, the width of the second flattened surface may be about 10 to 30 mm. In some other embodiments, the width of the first flattened surface may be about 10 to 30 mm, unless the surface encompasses the entire perimeter, or circumference of the male head component. In yet other embodiments, the height of the inner sidewall may range from about 5 mm to 10 cm.

Figure 8:
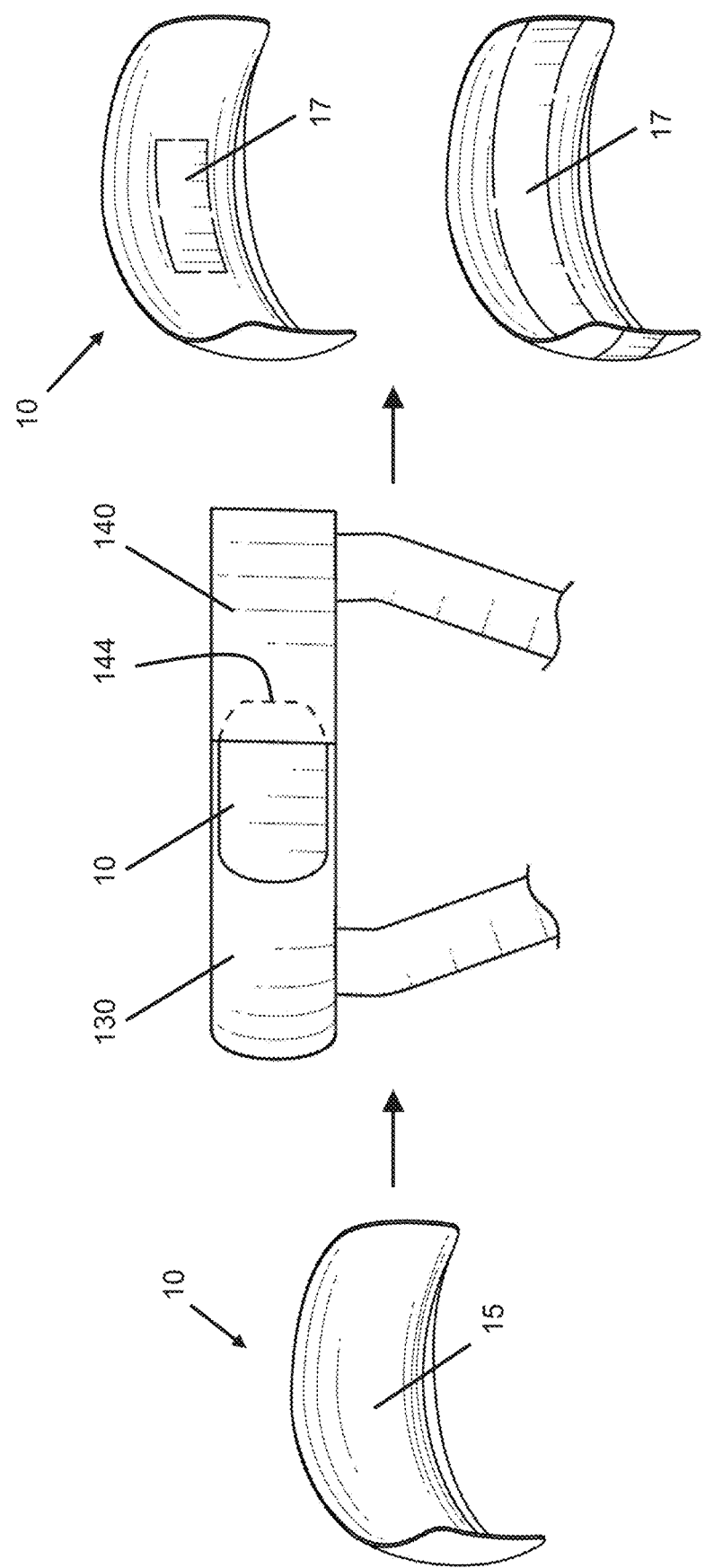
FIG. 8 shows a schematic of shaping a matrix band using the shaping tool of the present invention.
Figure 9:
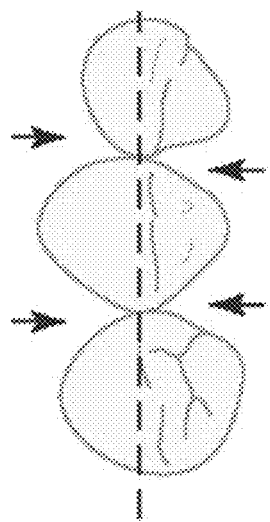
FIG. 9 is a diagram of teeth groups, wherein the arrows and dashed lines indicate points of contact between neighboring teeth.
Figure 9:
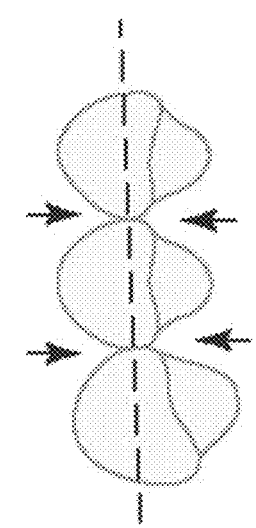

Since it has been a described a dental device for shaping a matrix band, it is another objective of the present invention to provide methods of utilizing the dental device. Referring now to FIG. 8, in one embodiment, the present invention features a method of shaping a matrix band (10). The method may comprise providing the dental device (100) described herein, pivoting the dental device (100) into the open configuration, and placing or positioning the matrix band (10) between the male head component (130) and the female head component (140) such that an inner surface (15) of the matrix band faces the inner sidewall (131) of male head component. Further still, the method comprises pivoting the dental device (100) into the closed configuration such that the matrix band (10) is interposed between the male head component (130) and the female head component (140) as the male head component (130) mates with the female head component (140), and applying pressure to the first and second handle portions (114, 124) so as to press the male head component (130) and the female head component (140) against each other. By compressing the matrix band between the head components, the matrix band (10) is shaped or formed to have i) a contour and curvature similar to that of the inner sidewall (141) of the female head component, and ii) a flattened surface (17) similar to the second flattened surface (144), the flattened surface (17) disposed on a midsection of the matrix band.

In some embodiments, any existing matrix band (10) may be shaped by the dental device (100) of the present invention. Examples of the matrix band include, but are not limited to, a metallic strip having a flat inner surface (15) prior to shaping or a metallic strip having a concaved inner surface (15) prior to shaping. The midsection of the matrix band is a central area disposed between the top and bottom edges of the band. Further still, the midsection may be disposed between the side edges of the band. In some preferred embodiments, the flattened surface (17) is formed and centrally disposed on at least the inner surface of the band. As shown in FIG. 8, the top right image shows the matrix band with a rectangular flattened surface, which may be formed using the head components according to the embodiment shown in FIGS. 4A and 4B. Alternatively or in addition, the matrix band can have a circular, oval or square flattened surface (not shown) that is formed using the head components according to the corresponding embodiments shown in FIGS. 7A-7F. In other embodiments, the bottom right image shows the matrix band with a rectangular flattened surface that can span the entire width (from side to side) of the matrix band, which may be shaped using the head components according to the embodiment shown in FIGS. 5A-5B or 6A-6B.

Figure 10:
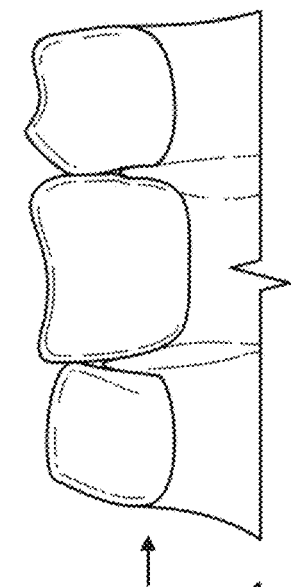
FIG. 10 is a schematic of restoring a tooth using a modified matrix band shaped using the shaping tool of the present invention.

According to another embodiment, the dental device (100) may be used during a tooth restoration procedure. In some embodiments, the present invention features a method of restoring a tooth having caries. Referring to FIG. 10, the method may comprise removing the caries from the tooth, thereby forming at least one cavity in the tooth, providing the dental device (100) described herein and shaping a matrix band with the dental device (100). The procedure for shaping the matrix band is consistent with the method previously described herein and provides a flattened surface (17) disposed on a midsection of the matrix band. After shaping the matrix band, the restoration method continues with placing the shaped matrix band (10) at least partially around the tooth so as to provide structural support to the cavity and filling the cavity with a dental filler material, which is allowed to cure and/or set. Preferably, the flattened surface (17) of the matrix band is positioned adjacent to a neighboring tooth. For example, the flattened surface (17) is positioned between the cavity and the neighboring tooth.

After the filler material has set and hardened, the matrix band (10) is removed, thereby leaving the restored tooth. Without wishing to limit the invention to a particular theory or mechanism, the flattened surface (17) of the matrix band provides a broad, flat surface to a restored portion of the tooth that contacts or is adjacent to the neighboring tooth. This broad flat surface can have increased stability as compared to a rounded point of contact, which can extend the lifetime of the restored portion.

As shown in the middle image of FIG. 8, when shaping the matrix band using the device of the present invention, the surface of the band can acquire a contour, taken from a cross-section between the top and bottom edges of the band at the midsection, comprising a first concave segment that transitions to a substantially straight segment, which transitions to a second concave segment. As shown in the middle image of FIG. 10, this contour of the matrix band allows for the restored portion of the tooth that is adjacent to the neighboring tooth to have a contour comprising a convex curvature near the occlusal surface that transitions to a substantially flat surface adjacent to the neighboring tooth, which transitions to a convex curvature in the apical direction.

As used herein, the term "about" refers to plus or minus 10% of the referenced number.

The disclosures of the following U.S. Patents are incorporated in their entirety by reference herein: U.S. Pat. Nos. 2,698,483, 4,081,909, US20040106084

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

Reference numbers recited in the below claims are solely for ease of examination of this patent application by the patent office only, are exemplary, and are not intended in any way to limit the scope of the claims to the particular features having the corresponding reference numbers in the drawings.

What is claimed is:

1. A dental device (100) for shaping a matrix band (10), said device (100) comprising:
   a. a first arm (110) comprising a first bar portion (112) connected to a first handle portion (114), and a first pivot point (116) disposed between the first bar portion (112) and the first handle portion (114);
   b. a second arm (120) comprising a second bar portion (122) connected to a second handle portion (124), and a second pivot point (126) disposed between the second bar portion (122) and the second handle portion (124);
   c. a male head (130) component disposed on a terminal end (113) of the first bar portion; and
   d. a female head component (140) disposed on a terminal end (123) of the second bar portion;
   wherein the first arm (110) is pivotably connected to the second arm (110) by a pivot (150) disposed through the first and second pivot points (116, 126), wherein the first and second arm (110, 120) can rotate about the pivot (150) between an open configuration and a closed configuration, wherein to place the device (100) in the open configuration, the first and second handle portions (114, 124) are pivoted away from each other thereby pivoting the first and second bar portions (112, 122) away from each other, wherein to place the device (100) in the closed configuration, the first and second handle portions (114, 124) are pivoted towards each other thereby pivoting the first and second bar portions (112, 122) toward each other,
   wherein the male head component has a curved, convex inner sidewall (131) facing a curved, concave inner sidewall (141) of the female head component, wherein the convex inner contour of the inner sidewall of the male head component matches the concave contour of the inner sidewall of the female head component when viewed from a side view,
   wherein a first flattened surface (134) is disposed on a midsection within the convex contour of the convex inner sidewall (131) of the male head component, and a second flattened surface (144) is disposed on a midsection within the concave contour of the concave inner sidewall (141) of the female head component, wherein the first flattened surface (134) is aligned with and facing the second flattened surface (144),
   wherein when the device (100) is in the closed configuration, the male head component (130) mates with the female head component (140) such that the curved, convex inner sidewall (131) of the male head component interfaces with the curved, concave inner sidewall (141) of the female head component, and the first flattened surface (134) of the male head component directly interfaces with the second flattened surface (144) of the female head component.

2. The device (100) of claim 1, wherein a gripping section (160) is disposed on the first and second handle portions (114, 124).

3. The device (100) of claim 1, wherein the male head component (130) is circular or oval in shape.

4. The device (100) of claim 1, wherein the terminal end (113) of the first bar portion is connected to a bottom surface (138) of the male head component.

5. The device (100) of claim 1, wherein the terminal end (123) of the second bar portion is connected to a bottom surface (148) of the female head component.

6. The device (100) of claim 1, wherein the first and second flattened surfaces (134, 144) are rectangular, square, circular, or oval in shape.

7. A method of shaping a matrix band (10), said method comprising:
   a. providing the dental device (100) of claim 1;
   b. pivoting the dental device (100) into the open configuration;
   c. placing the matrix band (10) between the male head component (130) and the female head component (140) such that an inner surface (15) of the matrix band faces the convex inner sidewall (131) of male head component;
   d. pivoting the dental device (100) into the closed configuration such that the matrix band (10) is interposed between the male head component (130) and the female head component (140) as the male head component (130) mates with the female head component (140); and
   e. applying pressure to the first and second handle portions (114, 124) so as to press the male head component (130) and the female head component (140) against each other, thereby shaping the matrix band (10) to have i) a contour and curvature similar to that of the convex inner sidewall (141) of the female head component, and ii) the first flattened surface (134) similar to the second flattened surface (144), the first flattened surface (134) is disposed on the midsection within the convex contour of the convex inner sidewall (131) of the male head component, and the second flattened surface (144) is disposed on the midsection within the concave contour of the concave inner sidewall (141) of the female head component, wherein the first flattened surface (134) is aligned with and facing the second flattened surface (144).

8. The method of claim 7, wherein the matrix band (10) is a metallic strip having a flat inner surface (15) prior to shaping.

9. The method of claim 7, wherein the matrix band (10) is a metallic strip having a concaved inner surface (15) prior to shaping.

* * * * *